US008108226B2

(12) United States Patent
Barrett et al.

(10) Patent No.: US 8,108,226 B2
(45) Date of Patent: *Jan. 31, 2012

(54) SYSTEM AND PROGRAM FOR ELECTRONICALLY MAINTAINING MEDICAL INFORMATION BETWEEN PATIENTS AND PHYSICIANS

(75) Inventors: D. Neale Barrett, San Jose, CA (US); Jennifer Eaton, Morgan Hill, CA (US); Joy Nakamura, San Jose, CA (US); Deanna M. Shaw, San Jose, CA (US)

(73) Assignee: International Business Machines Corporation, Armonk, NY (US)

( * ) Notice: Subject to any disclaimer, the term of this patent is extended or adjusted under 35 U.S.C. 154(b) by 995 days.

This patent is subject to a terminal disclaimer.

(21) Appl. No.: 12/046,311

(22) Filed: Mar. 11, 2008

(65) Prior Publication Data
US 2008/0154646 A1 Jun. 26, 2008

Related U.S. Application Data

(63) Continuation of application No. 09/513,859, filed on Feb. 28, 2000, now Pat. No. 7,542,911.

(51) Int. Cl.
*G06Q 10/00* (2006.01)
(52) U.S. Cl. .................. 705/2; 705/3; 705/4; 705/7.18; 600/300; 707/1
(58) Field of Classification Search ................. 705/2–4; 600/300
See application file for complete search history.

(56) References Cited

U.S. PATENT DOCUMENTS

| 4,695,954 A | 9/1987 | Rose et al. |
| 5,065,315 A | 11/1991 | Garcia |
| 5,772,585 A | 6/1998 | Lavin et al. |
| 5,823,948 A | 10/1998 | Ross, Jr. et al. |
| 5,832,488 A | 11/1998 | Eberhardt et al. |
| 5,867,821 A | 2/1999 | Ballantyne et al. |
| 5,877,975 A | 3/1999 | Jigour et al. |
| 5,923,759 A | 7/1999 | Lee |
| 5,924,074 A | 7/1999 | Evans |
| 5,978,262 A | 11/1999 | Marquot et al. |
| 5,995,965 A | 11/1999 | Experton |
| 6,000,608 A | 12/1999 | Dorf |
| 6,011,858 A | 1/2000 | Stock et al. |
| 6,014,631 A | 1/2000 | Teagarden et al. |

(Continued)

FOREIGN PATENT DOCUMENTS
DE 19701521 7/1998
(Continued)

OTHER PUBLICATIONS

IBM "Medical Advisor Function for Personal Computers", IBM Technical Disclosure Bulletin, vol. 37, No. 07, Jul. 1994, p. 625.

(Continued)

*Primary Examiner* — Vanel Frenel
(74) *Attorney, Agent, or Firm* — Janaki K. Davda; Konrad Raynes & Victor LLP (57) ABSTRACT

Disclosed is a method, system, program, and data structure for maintaining electronic patient medical information. An electronic patient data structure is generated to include patient biographical information and one of medical history information, medication schedule information, and appointment schedule information. The patient data structure is electronically transmitted between a physician computer and a portable patient device. The patient data structure is capable of being modified.

24 Claims, 5 Drawing Sheets

U.S. PATENT DOCUMENTS

| | | | |
|---|---|---|---|
| 6,032,119 | A | 2/2000 | Brown et al. |
| 6,034,621 | A | 3/2000 | Kaufman |
| 6,055,506 | A | 4/2000 | Frasca, Jr. |
| 6,101,478 | A | 8/2000 | Brown |
| 6,161,095 | A | 12/2000 | Brown |
| 6,167,379 | A | 12/2000 | Dean et al. |
| 6,277,071 | B1 | 8/2001 | Hennessy et al. |
| 7,542,911 | B2 | 6/2009 | Barret et al. |
| 2002/0181680 | A1 | 12/2002 | Linder et al. |

FOREIGN PATENT DOCUMENTS

| | | |
|---|---|---|
| EP | 0575230 | 12/1993 |
| FR | 2708343 | 2/1995 |
| FR | 2730330 | 8/1996 |
| FR | 2752316 | 2/1998 |
| FR | 2752317 | 2/1998 |
| WO | 9722092 | 6/1997 |
| WO | 9813783 | 4/1998 |

OTHER PUBLICATIONS

MediSoft Patient Accounting—Manual updates for Version 5 dated Aug. 1999 (H049 (to Version 5.5 dated Sep. 1999 (1309), 4 pages.

First Office Action dated Jul. 17, 2002, pp. 1-23, for U.S. Appl. No. 09/513,859 by inventors D.N. Barrett et al.

Response dated Oct. 28, 2002, pp. 1-29, to First Office Action dated Jul. 17, 2002, pp. 23, for U.S. Appl. No. 09/513,859 by inventors D.N. Barrett et al.

Final Office Action dated Jan. 7, 2003, pp. 1-15, for U.S. Appl. No. 09/513,859 by inventors D.N. Barrett et al.

Response Mar. 14, 2003, pp. 1-19, to Final Office Action dated Jan. 7, 2003, pp. 1-15, for U.S. Appl. No. 09/513,859 by inventors D.N. Barrett et al.

Third Office Action dated May 23, 2003, pp. 1-17, for U.S. Appl. No. 09/513,859 by inventors D.N. Barrett et al.

Response dated Aug. 29, 2003, pp. 1-18, to Third Office Action dated May 23, 2003, pp. 1-17, for U.S. Appl. No. 09/513,859 by inventors D.N. Barrett et al.

Second Final Office Action dated Nov. 17, 2003, pp. 1-24, for U.S. Appl. No. 09/513,859 by inventors D.N. Barrett et al.

Response dated Jan. 19, 2004, pp. 1-20, to Second Final Office Action dated Nov. 17, 2003, pp. 1-24, for U.S. Appl. No. 09/513,859 by inventors D.N. Barrett et al.

RCE and Amendment dated Feb. 3, 2004, pp. 1-17, to Second Final Office Action dated Nov. 17, 2003, pp. 1-24, for U.S. Appl. No. 09/513,859 by inventors D.N. Barrett et al.

Fifth Office Action dated Apr. 20, 2004, pp. 1-18, for U.S. Appl. No. 09/513,859 by inventors D.N. Barrett et al.

Response dated Jul. 19, 2004, pp. 1-20, to Fifth Office Action dated Apr. 20, 2004, pp. 1-17, for U.S. Appl. No. 09/513,859 by inventors D.N. Barrett et al.

Third Final Office Action dated Oct. 18, 2004, pp. 1-17, for U.S. Appl. No. 09/513,859 by inventors D.N. Barrett et al.

Appeal Brief dated Mar. 11, 2005, pp. 1-34, to Third Final Office Action dated Oct. 18, 2004, pp. 1-24, for U.S. Appl. No. 09/513,859 by inventors D.N. Barrett et al.

Second Appeal Brief dated Jun. 23, 2005, pp. 1-42, to Notice of Non-Compliant Appeal Brief dated May 25, 2005, pp. 1-3, for U.S. Appl. No. 09/513,859 by inventors D.N. Barrett et al.

Notice of Allowance Dec. 11, 2007, pp. 1-6, U.S. Appl. No. 09/513,859 by inventors D.N. Barrett et al.

SYSTEM AND PROGRAM FOR ELECTRONICALLY MAINTAINING MEDICAL INFORMATION BETWEEN PATIENTS AND PHYSICIANS

CROSS REFERENCE TO RELATED APPLICATIONS

This application is a continuation of and claims the benefit of U.S. Pat. No. 7,542,911, having application Ser. No. 09/513,859, filed on Feb. 28, 2000, the disclosure of which is incorporated herein by reference in its entirety.

BACKGROUND OF THE INVENTION

1. Field of the Invention

The present invention relates to a system, method, program for electronically maintaining medical information between patients and physicians and, in particular, where the information is maintained in a patient data structure that may be communicated between a physician computer and a patient device.

2. Description of the Related Art

Providing health care to patients who require considerable medical attention, such as elderly persons or those having debilitating illnesses, can be problematic on many fronts. For instance, when the patient visits a new physician, the patient must spend time filling out patient medical and prescription history and insurance information. For elderly or ill patients, this process can be difficult and often yields inaccurate or incomplete information. Further, the physician and staff must spend considerable time questioning the patient on past symptoms, illnesses, and current medications and therapies. Again, if the patient is elderly or somewhat incapacitated, then they will likely not be able to garner an adequate, let alone complete, picture of the patient's current state. This failure to provide the treating physician complete information may cause the physician to misdiagnose the patient's problem or prescribe inappropriate or redundant medications and therapies.

Still further, an elderly or ill patient may have trouble keeping track of all the medication they must take and the schedule for their medication, as well as remembering all their medical appointments. Further, a care taker who is responsible for assisting a patient on a daily basis may have difficulty keeping track of all appointments and medication schedules.

Currently, there are patient management database and scheduling software products tailored for a physician's office that are used to maintain patient information, including medical history, medication history, insurance billing information, and visit scheduling. However, currently, such information is maintained solely by the physician and such electronic information is not communicated to the patient or other physicians treating the patient in a separate clinic.

For these reasons, there is a need in the art for an improved patient medical information system that allows patient medical information, such as medical history, insurance information, prescription information, and visit scheduling to be effectively communicated to the patient, the care provider for the patient, and the different doctors and physician offices the patient must visit.

SUMMARY OF THE PREFERRED EMBODIMENTS

To overcome the limitations in the prior art described above, preferred embodiments disclose a method, system, and program for maintaining electronic patient medical information. An electronic patient data structure is generated to include patient biographical information and one of medical history information, medication schedule information, and appointment schedule information. The patient data structure is electronically transmitted between a physician computer and a portable patient device. The patient data structure is capable of being modified.

In further embodiments, the portable patient device comprises a portable computing device including a display. Views of the patient medication and appointment schedule information device stored in the patient data structure are displayed in the display of the portable computing device to allow the patient to review scheduled medication and appointments.

In still further embodiments, log information is generated indicating modifications to information in the patient data structure. The log information is read-only and once generated cannot be altered at the physician computer or within the portable patient device.

Still further, the physician computer may add one of appointment and medication events to the patient data structure. One appointment event indicates a scheduled visit at the physician office and one medication event indicates a drug prescription. The physician computer may transmit the modified patient data structure to the patient device.

Preferred embodiments provide a medical information system that allows a patient to maintain a patient data structure including detailed patient biographical, insurance, and medical history information. This allows the patient to visit a physician's office for a first time without having to fill out the registration forms as all the information the physician needs is provided in the patient data structure, which is electronically transmitted from the portable patient device to the physician computer. Further, neither the patient nor physician have to spend time discussing the patient's medical history and current medications and therapies, as such information would be embedded in the patient data structure. This not only saves time, but allows the physician to provide a faster and more accurate diagnosis because the physician has access to detailed medical history information. This is especially important if the patient is physically or mentally impaired and cannot answer the physician's questions accurately.

Further, preferred embodiments provide medication and appointment scheduling information which the patient can easily access to determine their medication and appointment schedule. The physician may access the patient's medication and appointment schedules to determine current medications the patient is taking and the patient's schedule for the purpose of avoiding scheduling a conflicting appointment or medication.

Still further, the use of the unalterable, read-only log information ensures data integrity because any attempts by either the patient or physician to improperly modify patient medical information are logged and, thus, can be detected.

BRIEF DESCRIPTION OF THE DRAWINGS

Referring now to the drawings in which like reference numbers represent corresponding parts throughout.

DETAILED DESCRIPTION OF THE PREFERRED EMBODIMENTS

In the following description, reference is made to the accompanying drawings which form a part hereof and which illustrate several embodiments of the present invention. It is understood that other embodiments may be utilized and structural and operational changes may be made without departing from the scope of the present invention.

Figure 1:
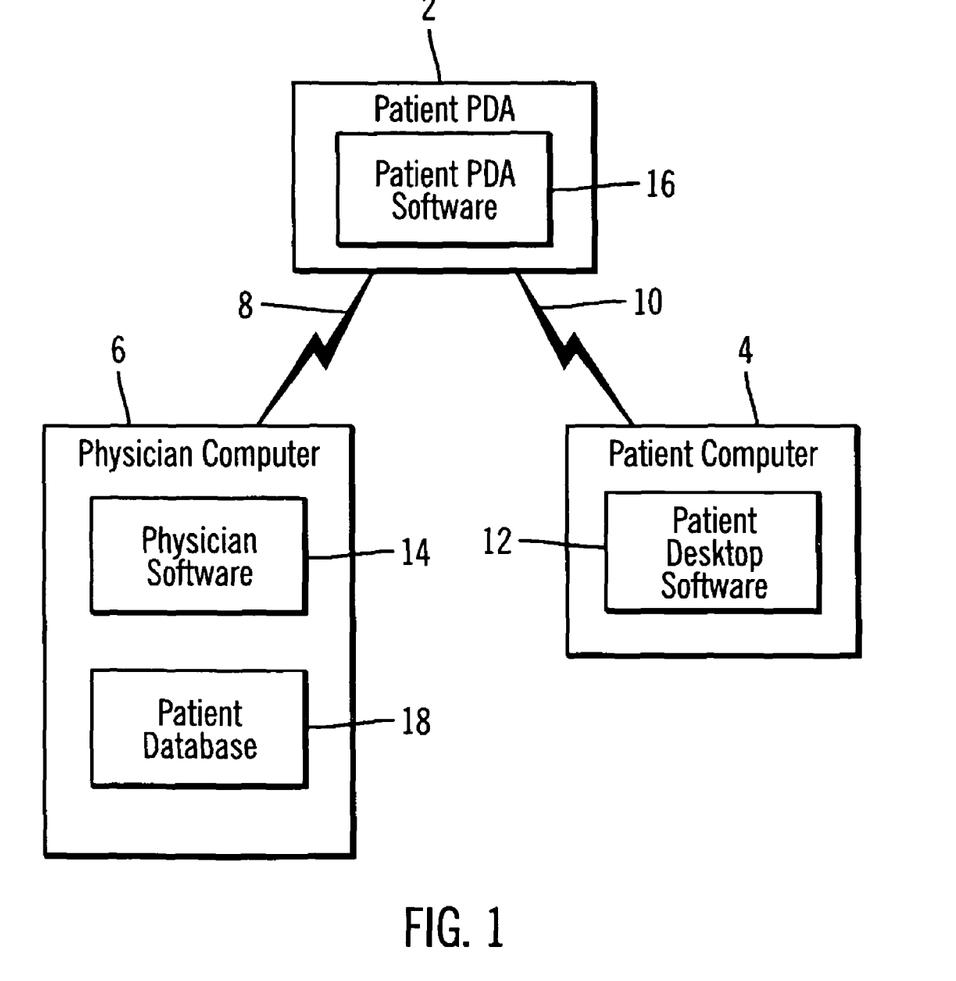
FIG. 1 illustrates a computing environment in which preferred embodiments are implemented.

FIG. 1 illustrates a computing environment in which preferred embodiments are implemented. A patient portable personal digital assistant (PDA) 2 is capable of communicating with a patient computer 4 and with a physician computer 6 at the physician's office. The physician computer 6 may be part of a local area network (LAN) at the physician's office that connects to a computer including a patient database. The patient PDA 2 may be any portable PDA type or similar device known in the art, including palm and handheld PDAs, such as the PalmPilot products from 3COM., Hewlett-Packard Company's Jornada 820, 680/690 and 430se, Psion Revo, IBM WorkPad, Cassiopeia from Casio Computer Co., Ltd, etc. The patient PDA 2 may include an interactive display as well as an input technology, such as a pen stylus and touch screen display input, voice input, keyboard, displayed keyboard, etc.

**PalmPilot is a trademark of 3COM Corporation; WorkPad is a registered trademark of the IBM Corporation; Revo is a trademark of Psion Enterprise Computing Ltd.

The patient PDA 2 may establish communication links 8, 10 with the physician 6 and patient 4 computers, respectively. The communication links 8, 10 may be implemented using any PDA/computer communication technology known in the art, such as infrared communication, serial, parallel, etc. For instance, the computers 4, 6 and patient PDA 2 may include infrared communication ports to communicate data therebetween. Alternatively, a cradle capable of mating with the patient PDA 2 may be attached to the computers 4, 6 via a serial port. The patient PDA 2 may be placed into the cradle to allow data transfer between the patient PDA 2 and computers 4, 6.

The patient computer 4 includes patient desktop software 12, the physician computer 6 includes physician software 14, and the patient PDA 2 includes patient PDA software 16. These software programs 12, 14, and 16 allow the sharing of medical information between a patient and physician computing devices to facilitate the transfer of medical information and assist the patient in maintaining scheduling of medication and physician visits. The physician computer 6 further includes a patient database 18, which comprises database records for all patients.

Figure 2:
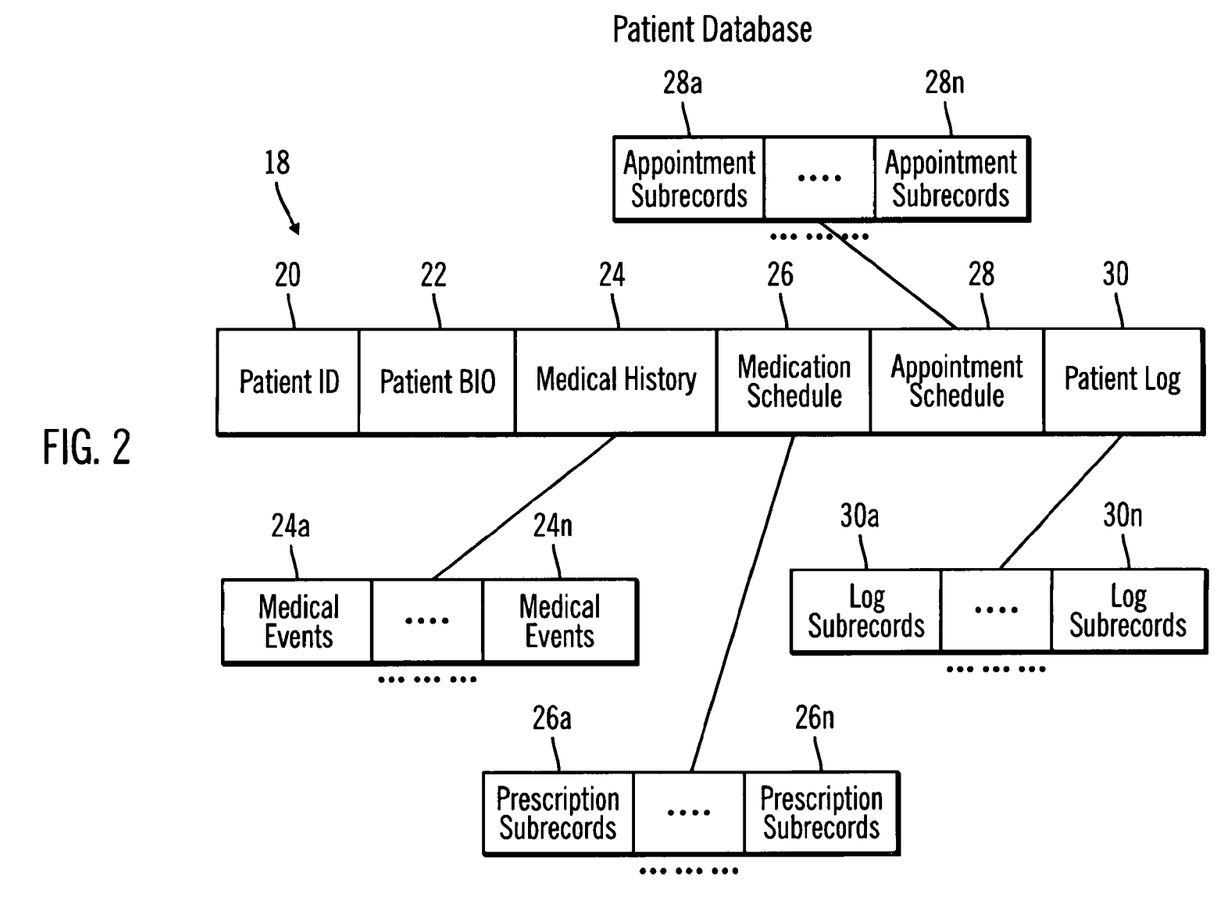
FIG. 2 illustrates an arrangement of patient information in a patient record in accordance with preferred embodiments of the present invention.

In preferred embodiments, patient medical information is maintained as database records. FIG. 2 illustrates a preferred embodiment of a data structure for a patient record 18*i* in the patient database 18. The patient database 18 is comprised of patient records 18*i* for each patient the physician is treating. A patient record includes the following fields:

Patient ID 20: Unique identifier of patient, such as social security number, providing the key column for patient records in the patient database 18.

Patient Bio 22: This field is comprised of subfields including biographical information of the patient, such as full name, social security number, current address, sex, family contact information, insurance billing information, etc.

Medical History 24: This field is comprised of a string of one or more medical event subrecords 24*a*-24*n*. A medical event subrecord is created upon the occurrence of a medical event, such as an illness, routine check-up or other event resulting in a consultation with a physician. Each medical event subrecord would include fields for the date of the medical event, diagnosis, prescribed medication, hospitalization, length of symptoms, outcome, treating physician, etc.

Medication Schedule 26: This field is comprised of a string of one or more current prescription subrecords 26*a*-26*n*. A prescription subrecord is created whenever a doctor prescribes medication. Each prescription subrecord would include fields for the date of prescription, dosage schedule, number of refills, prescribing physician, reason for prescription, and whether the prescription was filled and taken as scheduled. Fields may also be maintained for the patient to indicate whether they took a dosage to allow both the physician and patient to determine whether the patient has been taking the prescribed medication. Further, there may be a pharmacist field indicating whether the subscription was filled. Still further an alarm function may be provided to allow the patient to set an alert to activate at a scheduled medication time and notify the patient of the scheduled event. This notification function could use existing alarm functions in the system (e.g., patient PDA 2, patient 4 and physician 6 computers) or any other alarm/scheduling software routine known in the art to schedule and generate an alarm notification. In preferred implementations, the patient PDA software 16 could not modify the pharmacist field as well as the information in the prescription subrecords 26*a*-26*n* entered by the physician.

Appointment Schedule 28: This field is comprised of one or more appointment subrecords 28*a*-28*n*. Each appointment subrecord includes fields for the date of the appointment, physician name, reason for appointment, etc. Again, an alarm function may be provided to allow the patient to set an alarm to activate to alert the patient of a scheduled appointment.

Patient Log 30: This field is comprised of one or more log subrecords 30*a*-30*n*. Each log subrecord logs any additions, deletions or modifications to any field or subrecord of patient information. Each log subrecord indicates the date of change to the patient information, person or entity making change (e.g., patient or physician), key to record being changed, and change made. All the software programs 12, 14, and 16 that are capable of modifying a patient record 18*i* would include the capability to automatically write an entry to the log record whenever information in the patient record 18*i* is modified. For security reasons and to ensure the integrity of patient information, patient log records are read-only such that neither the physician software 14, patient desktop software 12, patient PDA software 16 nor any other text editor or program can modify the log subrecords.

This ensures that no one can change any patient information without such change being recorded in an unalterable record. Thus, a doctor cannot alter the patient log 30 to reverse any wrongful entries nor can the patient modify records to hide medical diagnosis, alter prescriptions, etc. This read-only feature of the patient log 30 ensures data integrity and accuracy of the information in the medical system.

The patient database 18 includes patient records 18i for multiple patients. The patient PDA 2 and patient computer 4 would maintain one patient record, including sub-records 20-30. Further, people may additionally store another person's patient record (e.g, a child, relative, friend, or recipient of paid-for-care) in their own patient PDA for convenience when acting as a care giver on behalf of another. The patient PDA 2 would communicate the patient record to the physician computer 6 and patient computer 4 via the communication links 8 and 10, respectively. The software programs 12, 14, and 16 provide the physician and patient views to the information in the patient record and an interface to alter fields and sub-records of the patient record.

Figure 3:
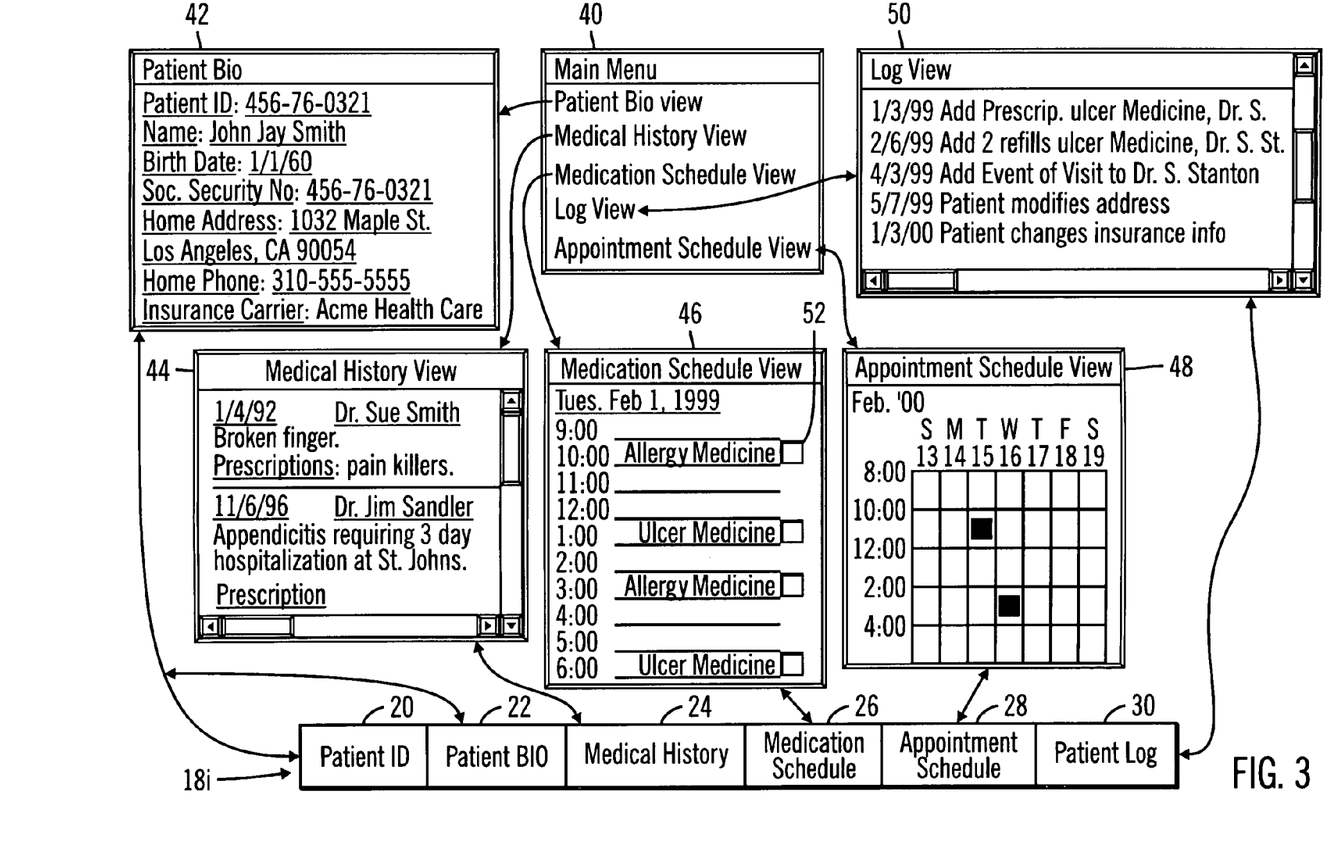
FIG. 3 illustrates different displayed views of patient information from information maintained in the patient record in accordance with preferred embodiments of the present invention.

FIG. 3 illustrates the views that may be displayed in the patient PDA 2 by the patient PDA software 16 and how such views relate to the patient record 18i. Upon selecting the medical information program using the patient PDA 2 graphical user interface (GUI), the patient would view the main menu 40 displayed in the PDA 2 GUI window. From this main menu 40, the patient may select one of five views: the patient bio view 42, the medical history view 44, the medication schedule view 46, the appointment schedule view 48, and the log view 50. Selection of one of the five displayed options on the patient PDA 2 using a pen stylus or other input device would cause the selected view 42, 44, 46, 48, 50 to be displayed on the patient PDA 2 display screen.

The patient bio view 42 displays subfields from the patient ID 20 and patient bio 22 fields in the patient record 18i. The medical history view 44 displays the medical event subrecords in the medical history field 24 of the patient record. The medical history view 44 may provide horizontal and vertical scrollable bars to allow the user to selectively scroll to view all the displayed fields in each medical event subrecords and all the medical event subrecords. The medication view 46 provides a calender display of a medication schedule, i.e., when to take prescribed medication, which is derived from the prescription subrecords 26a-26n in the medication schedule field 26 of the patient record 18i. Next to each scheduled medication dosage is a check box, e.g., check box 52, in which the patient can indicate that they took the scheduled dosage. Further, an alarm can be set to activate at the time of the scheduled dosage to alert the user of the scheduled event.

The medication view 46 shows a daily schedule of when to take medicine during the indicated day. View 48 is an example of a weekly view, in which a cell for each day of a week is displayed. The cells that include a block indicate a scheduled event, such as medication to take or a doctor appointment. Selection of the blocked cell may cause the display of a daily schedule providing further details of the scheduled event. A monthly schedule would provide a grid displaying a cell for each day of the month. A marker would be placed in the cell indicating an event scheduled for that day. Selection of the day cell would cause the display of a daily schedule providing details of scheduled events for the day.

The appointment view 48 displays a weekly, monthly or daily schedule of scheduled doctor visits that is derived from the appointment subrecords 28a-28n in the appointment schedule field 28. Again, an alarm may be set to activate to alert the user of scheduled appointments, such as an alarm set a couple of hours prior to the appointment, the day before the appointment, etc. The log view 50 displays the read-only log subrecords 30a-30n indicating changes made to any of the other fields and/or subrecords in the patient record.

The patient desktop software 12 would include GUI panels to allow a user to modify and edit information in a patient record. Similarly, the physician software 14 would provide GUI panels to allow a member of the physician's staff to edit information in any field and/or subrecord of a patient record 18i. As discussed, the physician computer 6 maintains a patient database 18 including a plurality of patient records 18i. The physician software 14 may be used to edit any patient record 18i. Moreover, the physician software 14 may provide the display of an appointment schedule that displays scheduled appointments for all patient records 18i in the patient database 18. This would be accomplished by locating in each patient record 18i the appointment subrecord 28i for that physician. In this way, the physician software 14 may include a scheduling tool to allow the physician's staff to manage appointments for all patients. The patient PDA software 16 would include the capability to allow a user to modify fields and/or subrecords from the patient record 18i displayed in the views 42-50 using the patient PDA 2 input. As discussed, all the software programs 12, 14, and 16 would automatically update the patient log 30 with an entry (log subrecord) whenever the patient or physician modify, add or delete information in the patient record 18i. Such log events cannot be altered, thereby ensuring the integrity of the data in the patient records.

The medical event, prescription, appointment, and log subrecords in the patient record 18i may be generated at different physician offices, wherein the physician offices include an installed version of the physician software 14 to modify and manipulate patient records.

If the non-volatile storage of the patient PDA 2 is limited, then it may not be possible to store all patient subrecords. In such case, using a criteria such as the age of subrecords or PDA storage capacity reaching a certain threshold, the patient PDA software 16 may prompt the user to archive subrecords to ensure that the patient PDA 2 does not run out of storage. The patient may archive the subrecords in a portable, non-volatile storage medium, such as a floppy disk or specialized storage module that is matable with the patient PDA 2. Alternatively, the patient may archive subrecords in the patient computer 4. In such case, the patient may provide the physician archived information on a separate non-volatile storage medium or via e-mail from the patient computer 4 to provide the physician the complete patient medical information.

Figure 4:
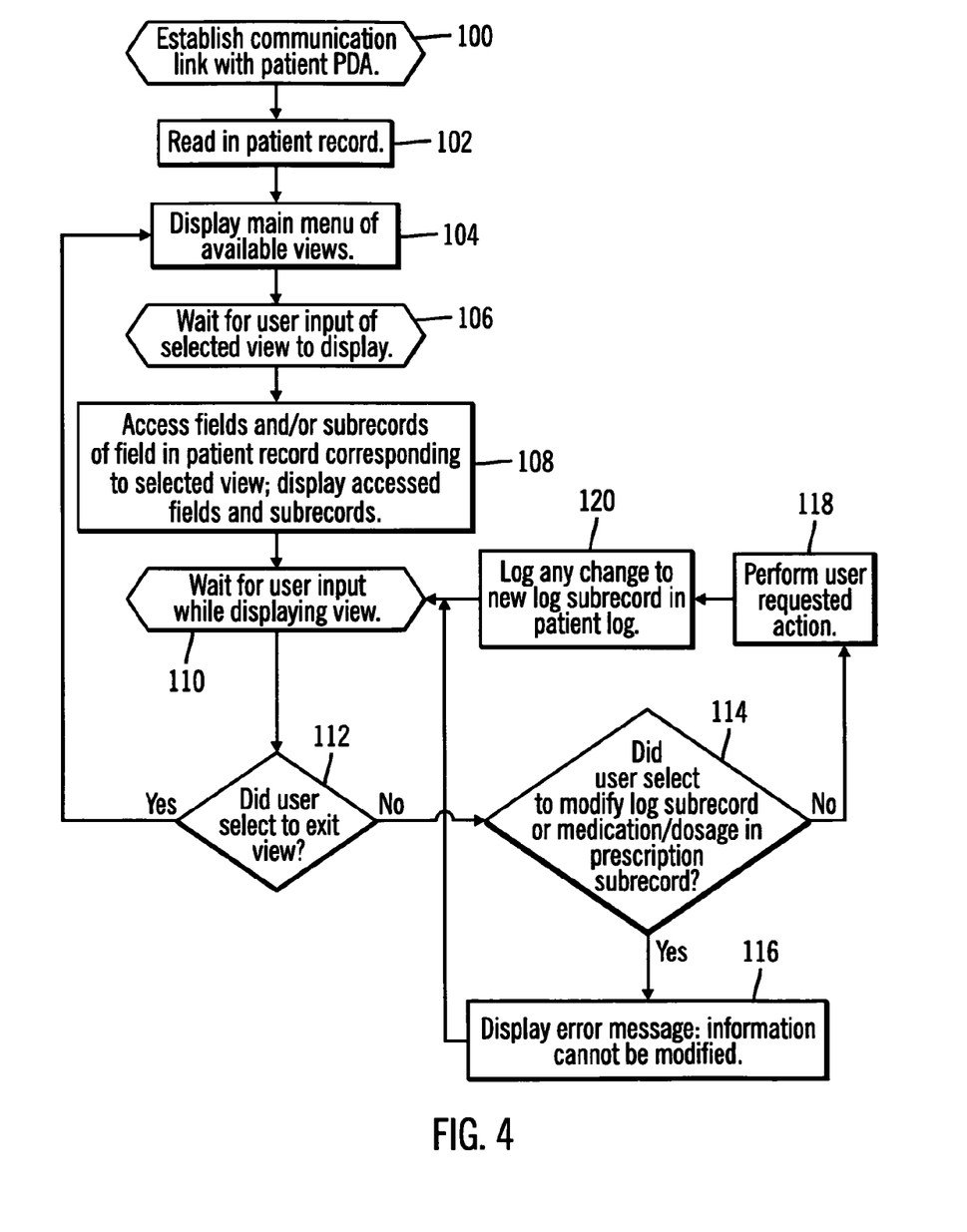
FIG. 4 illustrates logic implemented in a patient computer and patient personal digital assistant (PDA) device to manipulate and view patient information within a patient record in accordance with preferred embodiments of the present invention.

FIG. 4 illustrates logic implemented in the patient desktop software 12 to manipulate a patient record 18i and, in particular, handle the display and modification of information displayed in the views 42-50. The patient desktop software 12 would display in GUI panels on the display of the patient computer 4 the data displayed in the views 42-50 described with respect to the patient PDA 2. However, when the patient computer 4 is a desktop or laptop system, it has a display that is capable of displaying more information than the patient PDA 2, and thus the layout of the views 42-50 would be different than the layout shown with views 42-50 displayed on the patient PDA 2 as shown in FIG. 3. With respect to FIG. 4, control begins at block 100 with the patient desktop software 12 establishing a communication link with a patient PDA 2 and downloading a patient record. A password may be required to access a patient record. The patient computer 4 then reads the patient record over the communication link 10 into memory. Alternatively, the patient desktop software 12 may read the patient record from a storage location in the patient computer 4. After reading the patient record 18*i* into memory, the patient desktop software 12 displays (at block 104) a main menu of selectable views, such as shown in main menu view 40 in FIG. 3.

Upon receiving a user selection of a view (at block 106), the patient desktop software 12 (at block 108) accesses the fields and/or subrecords from the field in the patient record corresponding to the selected view and displays the accessed information in a GUI interface panel of the patient computer 4 and awaits user input (at block 110). If the user selected to exit the view (at block 112), then control proceeds back to block 104 to display the main menu of selectable views. Otherwise, if the user selected to modify a log subrecord 30*i* or a medication quantity or dosage in a prescription subrecord 26*i* (at block 114), then the patient desktop software 12 would display (at block 116) an error message on the patient computer 4 display that the information cannot be modified. Otherwise, the patient desktop software 12 performs (at block 118) the requested action, which may be to edit, modify, add, delete or further view information in the selected view being displayed. If the user action was to add, delete or modify any patient information in the patient record 18, then a log subrecord is created and added (at block 120) to the patient log 30 to log such change. From block 116 or 118, control returns to block 110 to wait for further user action.

Also, at any time, the user at the patient computer 4 can update the patient record 18*i* with any changes made. The patient computer 4 can further transfer a modified patient record 18*i* to the patient PDA 2 for storage therein. The advantage of this approach is that the patient may more conveniently edit patient information, such as the patient bio 22 fields, at a desktop or laptop patient computer 4 than a patient PDA which typically has a limited input mechanism, as opposed to the full keyboard available with desktop and laptop computers. Another advantage of using the patient desktop software 12 is that in the event the patient PDA 2 is lost or stolen, the patient would have a backup copy of the patient record 18*i* in the patient computer 4 to upload into a new patient PDA 2.

The patient PDA software 16 performs the same viewing operations described with respect to blocks 104-116 in FIG. 4 with respect to the patient desktop software 12.

Figure 5:
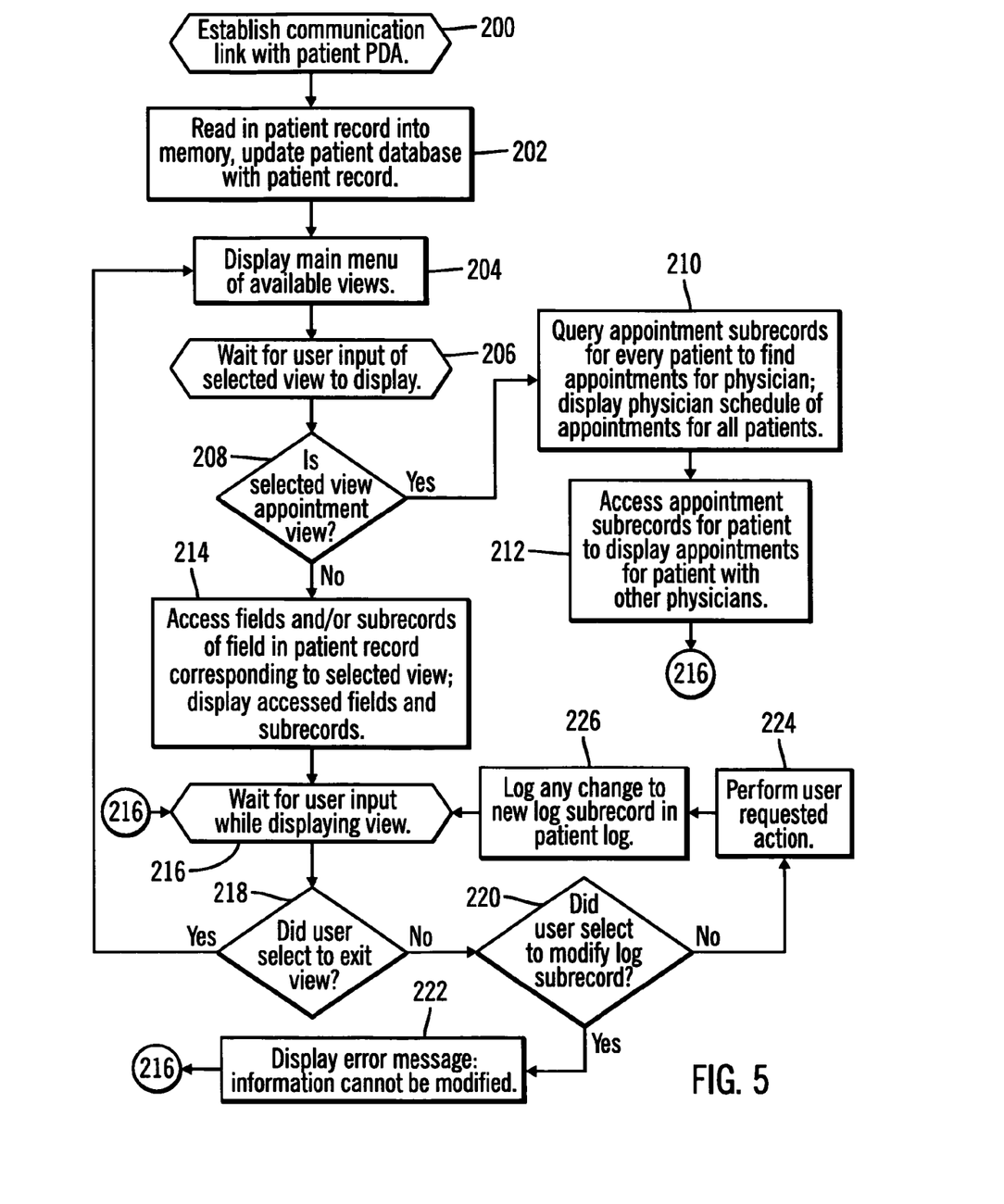
FIG. 5 illustrates logic implemented in a physician computer to manipulate and view patient information within a patient record in accordance with preferred embodiments of the present invention.

FIG. 5 illustrates logic implemented in the physician software 14 to interact with the patient PDA 2 and obtain and update a patient record 18*i*, and display views of the patient record. The physician software 14 performs many of the same operations as the patient desktop software 12 to interact with the patient PDA 2 and display views of the patient record 18*i*, with a few exceptions. One difference is that when displaying the appointment view, the physician software 14 displays (at blocks 210 and 212) appointments in the subrecords for all the patient records 18*i* in the patient database 18 as well as the appointments the current patient has with other physicians. This ensures that the physician staff member scheduling the appointment will not schedule an appointment that conflicts with appointments both the physician and patient have already made. Further, unlike the patient software 12 and 16, the physician software 14 allows the physician to modify prescription subrecords 26*a*-26*n* to electronically write patient prescriptions. In further embodiments, the physician software 14 may include the capability to digitally sign or encrypt a prescription with the physician public key so that the pharmacist can authenticate an electronic prescription within a prescription subrecord 26*a*-26*n* received from the patient PDA 2.

At any time the physician software 14 may update the patient database 18 with any changes made to a patient record 18*i* and then transmit the updated record to the patient PDA 2.

There are many advantages to the medical information system of the preferred embodiments. First, is that a patient may use the ubiquitous PDA device to maintain all the information needed to optimize a visit with a doctor. The patient PDA makes the first time visits to a doctor's office much easier because the patient does not have to fill out any forms. Instead, a communication link 8 is used to transmit the electronic patient record from the patient PDA 2 to the physician computer 6, without any involvement on behalf of the patient, except making the PDA 2 available. The physician's staff can then automatically obtain accurate personal and insurance billing information. This is especially helpful if the patient is ill or injured and cannot accurately respond or if the patient's care giver does not have such information available. Still further the physician can obtain detailed patient medical history, current prescriptions, and current scheduled medical appointments without relying on the mental capacities of the patient as such information is embedded in the patient record stored in the patient PDA 2. This aspect is especially important because the physician, by having accurate medical history and current treatment information, will reach the correct diagnosis faster and avoid prescribing any treatments or medications that could be duplicative or harmful to the patient. Still further, the physician can be assured of the integrity of the information as any attempts by the patient to falsify or improperly modify the medical history can be detected from the information displayed in the log view 50.

The advantages of the preferred embodiment medical information system are numerous. No longer must a patient spend time filling out tedious and time consuming forms. Instead, all the patient must do is allow a communication link 8 to be established so the patient record 18*i* can be transferred from the patient PDA 2 to the physician computer 6. Further, if the patient has a complex medical illness requiring numerous medications that may affect mental and memory capabilities, such as AIDS or cancer, then they may readily determine their medication schedule and any pending physician appointments from the medication 46 and appointment 48 schedule views. No longer must they remember to keep the handwritten appointment reminder cards doctors provide, which are oftentimes lost or misplaced. Further, patients may download their patient record 18*i* to a personal computer, i.e., the patient computer 4, where they may review and edit their schedules 46 and 48 from their desktop or laptop at home or work. To interface with their medical information, all they need do is install the patient desktop software 12 on the desktop or laptop system. Further, they may want to use their patient computer 6, which typically has an easier to use input mechanism, such as a full keyboard, to edit medical information.

The preferred embodiment medical information system is especially helpful to care givers who provide daily assistance to a disabled patient, such as an elderly or incapacitated person. Such patients are often unable to have or remember all the information the physician's office needs. The PDA software 12 can provide substantial assistance to the care giver in keeping track of all schedules appointments and medications. Further, the care giver when taking the patient to a new doctor need only make the patient PDA 2 available to electronically transfer the patient record 18*i* to provide the physician's office with all the information they need to register the patient.

Moreover, by providing the check boxes with the medication schedule view 46 to allow the patient to indicate that a dosage was taken and the alarm notification for scheduled medication, the patient does not have to worry about forgetting whether they took all their medication. Further, the physician can review the check boxes to determine whether the patient has in fact been taking their medication.

Insurance companies may also benefit from the preferred embodiment medical information system. To submit claims, all the patient or doctor need do is to electronically submit the medical event 24*i* subrecord or prescription subrecord 26*i* to the insurance company, thereby providing a paperless and automatic claim submittal system. Still further, the insurance company can detect fraud from discrepancies in the patient and physician version of a patient record 18*i*. This aspect of the preferred embodiments in improving efficiency to the physician and insurance company in processing claims and patient medical information, and in optimizing the patient registration and diagnosis process, will further reduce costs and improve both physician and insurance company profitability and, at the same time, provide patients better service.

CONCLUSION

The preferred embodiments may be implemented as a method, apparatus or article of manufacture using standard programming and/or engineering techniques to produce software, firmware, hardware, or any combination thereof. The term "article of manufacture" (or alternatively, "computer program product") as used herein is intended to encompass one or more computer programs and/or data files accessible from one or more computer-readable devices, carriers, or media, such as magnetic storage media, "floppy disk," CD-ROM, optical disks, holographic units, volatile or non-volatile electronic memory, etc. Further, the article of manufacture may comprise the implementation of the preferred embodiments in a transmission media, such as a network transmission line, wireless transmission media, signals propagating through space, radio waves, infrared signals, etc. Of course, those skilled in the art will recognize many modifications may be made to this configuration without departing from the scope of the present invention.

In the preferred embodiments, there were three described computing devices, patient PDA, patient computer, and physician computer. In further embodiments, additional computers may be added to the system. For instance, the patient may maintain a smart card to store the patient records. The physician would maintain a smart card reader to access the patient record in the card. In this way, if the patient cannot afford a PDA device, then the insurance company may provide a smart card to facilitate transfer of patient information to the physician's office thereby improving physician efficiency and reducing cost overhead. Still further, the patient may maintain a smart card reader at their computer to read information from the smart card to view at their personal computer. Yet further, newer smart card devices include limited displays. With such smart cards, the patient could review their medication and appointment schedule on the smart card display. Thus, any portable electronic device capable of providing non-volatile storage of a patient record may be used in place of the patient PDA 2 for the patient to take to a physician office, including those that do not include a display.

Preferred embodiments described specific views of patient medical and personal information as including specific fields of information. However, in alternative embodiments, different information may be presented in the above described views and further views may be provided to provide alternative views of patient medical and personal information.

Preferred embodiments described the patient record as comprised of fields, where the fields include further subfields and/or subrecords. However, those skilled in the design of database structures may realize that alternative database structures may be provided to represent the patient records. For instance, the patient record may be comprised of keys that index into other tables that include records for what is above described as included in a subrecord. For instance, a medical history table may store zero or more medical event records for a single patient record, thereby providing a one-to-many relationship between each patient record and medical event records in the medical history table. A similar table arrangement may be provided for the medication schedule and appointment schedule which is comprised of separate prescription and appointment records such that there is a relationship of patient records and prescription and appointment records in a medication and appointment tables. In such alternative embodiments, a patient record is comprised of multiple records, such as a patient bio record, and further records for medical events, prescriptions, appointments, and log events.

The preferred logic of FIGS. 4 and 5 described specific operations occurring in a particular order. In alternative embodiments, certain of the logic operations may be performed in a different order, modified or removed and still implement preferred embodiments of the present invention. Moreover, steps may be added to the above described logic and still conform to the preferred embodiments.

In summary, preferred embodiments disclose a method, system, and program for maintaining electronic patient medical information. An electronic patient data structure is generated to include patient biographical information and one of medical history information, medication schedule information, and appointment schedule information. The patient data structure is electronically transmitted between a physician computer and a portable patient device. The patient data structure is capable of being modified.

The foregoing description of the preferred embodiments of the invention has been presented for the purposes of illustration and description. It is not intended to be exhaustive or to limit the invention to the precise form disclosed. Many modifications and variations are possible in light of the above teaching. It is intended that the scope of the invention be limited not by this detailed description, but rather by the claims appended hereto. The above specification, examples and data provide a complete description of the manufacture and use of the composition of the invention. Since many embodiments of the invention can be made without departing from the spirit and scope of the invention, the invention resides in the claims hereinafter appended.

What is claimed is:

1. A medical information system for maintaining electronic patient medical information for use in a physician computer and a portable patient device, the physician computer comprising:

a computer-readable medium including one electronic patient data structure consisting of patient identification information, patient biographical information, medical history information including medical event information, medication schedule information, appointment schedule information, and log information;

at least one communication port for transmitting the patient data structure to the portable patient device and receiving the patient data structure from the portable patient device;

displaying, in the display of the portable computing device, a main menu of selectable views, wherein the selectable views consist of a patient bio view, a medical history view, a patient medication schedule view, an appointment schedule view, and a log view, and wherein the appointment schedule view displayed in the display of the portable computing device differs from the appointment schedule view that is displayable on a display at the physician computer, and wherein direct selection of one of the selectable views results in that selected view being displayed independently of the other selectable views; and means for modifying information in the patient data structure via at least one of the patient bio view, the medical history view, the patient medication schedule view, and the appointment schedule view, wherein the modified patient data structure is transmitted to the portable patient device via the communication port.

2. The system of claim 1, wherein the physician computer further comprises:

means for displaying the patient medication schedule view and the appointment schedule view stored in the patient data structure to allow the physician to review scheduled medication and appointments.

3. The system of claim 2, wherein the physician computer further comprises means for generating log information indicating modifications to information in the patient data structure, wherein the log information is read-only and once generated cannot be altered.

4. The system of claim 2, wherein the physician computer further comprises:

means for adding one of appointment and medication events to the patient data structure, wherein one appointment event indicates a scheduled medical related visit and one medication event indicates a drug prescription, wherein the drug prescription is digitally signed; and transmitting, via the communication port, the modified patient data structure to the portable patient device.

5. The system of claim 1, wherein the physician computer further comprises:

means for storing patient data structures for multiple patients;

means for displaying an interactive schedule of patient appointments from appointment schedule information maintained in the patient data structures, wherein appointment events are added to one patient data structure through the displayed interactive schedule of patient appointments, and wherein the displayed interactive schedule of patient appointments displays scheduled appointments for all patient records.

6. The system of claim 1, wherein the patient data structure further includes patient insurance billing information that the physician computer uses to generate insurance claims for patient services.

7. A medical information system for maintaining electronic patient medical information for use in a physician computer and a portable patient device, wherein the patient device includes:

a computer-readable medium including one electronic patient data structure consisting of patient identification information, patient biographical information, medical history information including medical event information, medication schedule information, appointment schedule information, and log information; and at least one communication port for transmitting the patient data structure to the physician computer and receiving the patient data structure from the physician computer, wherein the patient data structure is capable of being modified; and displaying, in the display of the portable computing device, a main menu of selectable views, wherein the selectable views consist of a patient bio view, a medical history view, a patient medication schedule view, an appointment schedule view, and a log view, and wherein the appointment schedule view displayed in the display of the portable computing device differs from the appointment schedule view that is displayable on a display at the physician computer, and wherein direct selection of one of the selectable views results in that selected view being displayed independently of the other selectable views.

8. The system of claim 7, wherein the portable patient device further comprises:

means for indicating that one scheduled patient medication was taken, wherein the medication schedule view provides a calendar display of a medication schedule derived from prescription subrecords in a patient record; and means for storing the indication in the patient data structure that the patient took the scheduled medication.

9. The system of claim 7, wherein the portable patient device further comprises means for setting an alarm to activate to provide an alert of one scheduled patient medication or appointment, wherein the alarm is set by a patient for whom the alert is scheduled and who is using the patient portable device.

10. The system claim 7, wherein the portable patient device further comprises means for generating log information indicating modifications to information in the patient data structure, wherein the log information is read-only and once generated cannot be altered.

11. The system of claim 7, wherein the patient data structure further includes patient insurance billing information that can be used to generate insurance claims for patient services.

12. The system of claim 7, further comprising an additional computer, wherein the additional computer includes:

means for transmitting the electronic patient medical information between the additional computer and the portable patient device, wherein the additional computer is capable of modifying information in the patient data structure via at least one of the patient bio view, the medical history view, the patient medication schedule view, and the appointment schedule view and transmitting the modified patient data structure to the portable patient device.

13. The system of claim 7, wherein the portable patient device comprises one of a smart card, palm computing device, hand-held computing device, and laptop computer.

14. An article of manufacture embodied on a computer-readable medium for use in a medical information system to maintain electronic patient medical information for use in a physician computer and a portable patient device, the article of manufacture including at least one computer program causing the physician computer to perform:

reading one electronic patient data structure consisting of patient identification information, patient biographical information, medical history information including medical event information, medication schedule information, appointment schedule information, and log information;

transmitting the patient data structure to the portable patient device;

receiving the patient data structure from the portable patient device;

displaying, in the display of the portable computing device, a main menu of selectable views, wherein the selectable views consist of a patient bio view, a medical history view, a patient medication schedule view, an appointment schedule view, and a log view, and wherein the appointment schedule view displayed in the display of the portable computing device differs from the appointment schedule view that is displayable on a display at the physician computer, and wherein direct selection of one of the selectable views results in that selected view being displayed independently of the other selectable views; and modifying information in the patient data structure via at least one of the patient bio view, the medical history view, the patient medication schedule view, and the appointment schedule view, wherein the modified patient data structure is transmitted to the portable patient device via the communication port.

15. The article of manufacture of claim 14, further causing the physician computer to perform:

displaying views of the patient medication and appointment schedule information stored in the patient data structure to allow the physician to review scheduled medication and appointments.

16. The article of manufacture of claim 14, further causing the physician computer to perform:

generating log information indicating modifications to information in the patient data structure, wherein the log information is read-only and once generated cannot be altered.

17. The article of manufacture of claim 14, further causing the physician computer to perform:

adding one of appointment and medication events to the patient data structure, wherein one appointment event indicates a scheduled medical related visit and one medication event indicates a drug prescription, wherein the drug prescription is digitally signed; and transmitting the modified patient data structure to the portable patient device.

18. The article of manufacture of claim 14, further causing the physician computer to perform:

storing patient data structures for multiple patients;

displaying an interactive schedule of patient appointments from appointment schedule information maintained in the patient data structures, wherein appointment events are added to one patient data structure through the displayed interactive schedule of patient appointments, and wherein the displayed interactive schedule of patient appointments displays scheduled appointments for all patient records.

19. The article of manufacture of claim 14, wherein the patient data structure further includes patient insurance billing information, further causing the physician computer to perform:

accessing the insurance billing information from the patient data structure to use in billing medical services to the patient's insurance company.

20. An article of manufacture embodied on a computer-readable medium for use in a medical information system to maintain electronic patient medical information for use in a physician computer and a portable patient device, the article of manufacture including at least one computer program causing the portable patient device to perform:

storing one electronic patient data structure consisting of patient biographical information and one of medical history information including medical event information, medication schedule information, and appointment schedule information;

transmitting the patient data structure to the physician computer;

receiving the patient data structure from the physician computer, wherein the patient data structure is capable of being modified; and displaying, in the display of the portable computing device, a main menu of selectable views, wherein the selectable views consist of a patient bio view, a medical history view, a patient medication schedule view, an appointment schedule view, and a log view, and wherein the appointment schedule view displayed in the display of the portable computing device differs from the appointment schedule view that is displayable on a display at the physician computer.

21. The article of manufacture of claim 20, further causing the patient device to perform:

indicating that one scheduled patient medication was taken, wherein the medication schedule view provides a calendar display of a medication schedule derived from prescription subrecords in a patient record; and storing the indication in the patient data structure that the patient took the scheduled medication.

22. The article of manufacture of claim 20, further comprising setting an alarm to activate to provide an alert of one scheduled patient medication or appointment, wherein the alarm is set by a patient for whom the alert is scheduled and who is using the patient portable device.

23. The article of manufacture of claim 20, further causing the patient device to perform:

generating log information indicating modifications to information in the patient data structure, wherein the log information is read-only and once generated cannot be altered at the physician computer or by the patient device.

24. The article of manufacture of claim 20, further causing the patient device to perform:

transmitting the electronic patient medical information to an additional computer, wherein the additional computer is capable of modifying information in the patient data structure via at least one of the patient bio view, the medical history view, the patient medication schedule view, and the appointment schedule view and transmitting the modified patient data structure to the portable device.

* * * * *

UNITED STATES PATENT AND TRADEMARK OFFICE
CERTIFICATE OF CORRECTION

| | | |
|---|---|---|
| PATENT NO. | : 8,108,226 B2 | Page 1 of 1 |
| APPLICATION NO. | : 12/046311 | |
| DATED | : January 31, 2012 | |
| INVENTOR(S) | : D. Neale Barret et al. | |

It is certified that error appears in the above-identified patent and that said Letters Patent is hereby corrected as shown below:

On the Title Page, Item (12): "Barrett" should read -- Barret --

On the Title Page, Item (75) Inventors: "D. Neale Barrett" should read -- D. Neale Barret --

Signed and Sealed this
Twenty-second Day of October, 2013

Teresa Stanek Rea
*Deputy Director of the United States Patent and Trademark Office*